United States Patent [19]

Lebreton et al.

[11] Patent Number: 5,686,405
[45] Date of Patent: Nov. 11, 1997

[54] METHOD OF FIXING A PERFUME IN A COSMETIC AND/OR DERMATOLOGICAL COMPOSITION WITH A PLANT COMPOUND

[75] Inventors: Francoise Lebreton, Bures-sur-Yvette; Didier Gagnebien, Chatillon, both of France

[73] Assignee: L'Oreal, Paris, France

[21] Appl. No.: 525,081

[22] Filed: Sep. 8, 1995

[30] Foreign Application Priority Data

Sep. 8, 1994 [FR] France ................................ 94 10764

[51] Int. Cl.⁶ .................................................. A61K 7/46
[52] U.S. Cl. ...................................... 512/2; 424/195.1
[58] Field of Search ..................... 512/2, 4; 424/195.1

[56] References Cited

FOREIGN PATENT DOCUMENTS

| | | |
|---|---|---|
| 673 630 | 12/1965 | Belgium . |
| 0 279 328 | 8/1988 | European Pat. Off. . |
| 0 345 075 | 12/1989 | European Pat. Off. . |
| 43 01 266 | 7/1994 | Germany . |
| 92 16195 | 10/1992 | WIPO . |

OTHER PUBLICATIONS

*Patent Abstracts of Japan*, vol. 4, No. 54, Apr. 23, 1980; JP 55 025456.

*Patent Abstracts of Japan*, vol. 9, No. 17, Jan. 24, 1985; JP 59 164711.

*Primary Examiner*—James H. Reamer
*Attorney, Agent, or Firm*—Oblon, Spivak, McClelland, Maier & Neustadt, P.C.

[57] ABSTRACT

The invention relates to a use of a method of fixing and/or prolonging release of a perfume in a cosmetic and/or dermatological composition with a plant compound, said plant compound comprising a plant extract and may be a mixture of plant gum and of plant extract.

16 Claims, 5 Drawing Sheets

METHOD OF FIXING A PERFUME IN A COSMETIC AND/OR DERMATOLOGICAL COMPOSITION WITH A PLANT COMPOUND

BACKGROUND OF THE INVENTION

1. Field of the Invention

The present invention relates to a method for fixing and/or prolonging release of a perfume in a cosmetic and/or dermatological composition with a plant compound. This composition can be used for the therapeutic treatment and/or in the case of the skin, both the face and the body or the hair, for cleansing the body and/or the hair, and for applying make-up to the skin, while perfuming them.

2. Discussion of the Background

It is recalled that a perfume is the combination of various fragrant substances. Each perfume has a top note which is the odor which is volatile to a greater or lesser degree and which is the first to diffuse during application or when the container containing it is opened, a medium note which corresponds to the complete perfume (emission for a few hours after the top note) and a base note which is the most persistent final note (emission for several hours after the medium note).

Human beings have always had the desire to use perfume, to perfume objects around them or the places where they live, to mask unpleasant odors as well as to give a nice odor and thus to have an olfactory satisfaction.

A number of products or compositions exist from which odors which are sometimes strong and/or unpleasant are released and which require the incorporation of perfume. Yet, depending on the nature of these products or compositions, it is not always easy to incorporate a perfume into them and/or to retain the pleasant olfactory effects.

Thus, document JP-A-03121169 teaches the persistence of a perfume in a printing ink by virtue of the use of a powder with a high adsorbent power, such as activated charcoal impregnated with perfume.

Unfortunately, in order to obtain perfumed ink, it is necessary to use a solid adsorbent material which should be removed before using the ink, thereby requiring a difficult operation and making the method of use cumbersome.

Moreover, a solid detergent, containing perfume which persists over time and which is gradually released during the various uses of the detergent, is also known from document JP-A-01101399. This detergent is obtained by first incorporating a perfume into an inorganic clay-organic composite and then mixing the perfumed clay with the detergent composition.

Unfortunately, the use of a clay in order to include a perfume in a detergent composition enhances the degradation of the perfume upon contact with heat or an alkaline agent present in the composition.

The use of hyaluronic acid or one of its salts in a perfume composition in order to give an enhanced stability to the latter is in addition known from document WO-A-8504803.

Unfortunately, hyaluronic acid has a perfume-fixing power which is still inadequate. In addition, its acidic functional group can cause irritations when it is brought into contact with skin.

It is also known from document WO-A-92/16195 that polysaccharide-based liquid crystals can encapsulate and deliver perfumes. However, these compounds do not allow sufficient fixing of the perfume.

Moreover, the use of the inner skin of oranges in a base in order to release a perfume slowly is also known from Patent Application JP-A-55 025456. However, this plant extract is not sufficiently effective for fixing the perfume correctly.

Consequently, there is still the need for a perfumed cosmetic and/or dermatological composition not having the above disadvantages and in particular, which does not require that solid compounds be incorporated into the perfume into the composition and/or to increase its stability without the latter becoming degraded in the long run, especially in contact with the other constituents of the composition.

The applicant has discovered surprisingly that the introduction of a plant compound in a perfumed composition allows the perfume not to become degraded and to persist for several hours on the subject or the object to be perfumed.

This composition allows in particular a prolonged release over time of the perfume during the use of this composition. In addition, in spite of successive openings of the bottle containing the composition, the later does not become degraded and, in particular, retains emission of the base note of the perfume until the bottle becomes empty.

SUMMARY OF THE INVENTION

To this end, the invention relates to a method for fixing and/or prolonging release of a perfume, in a cosmetic and/or dermatological composition, with a plant compound as agent, the plant compound comprising at least one non-film-forming and/or non-thickening plant extract and at least one plant gum.

The subject of the invention is also for fixing and/or prolonging release of a perfume in a cosmetic and/or dermatological composition with a plant compound, said plant compound comprising at least one plant extract selected from the group consisting of fucus, lichen, borage, almond, marshmallow and linseed extracts and mixtures thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
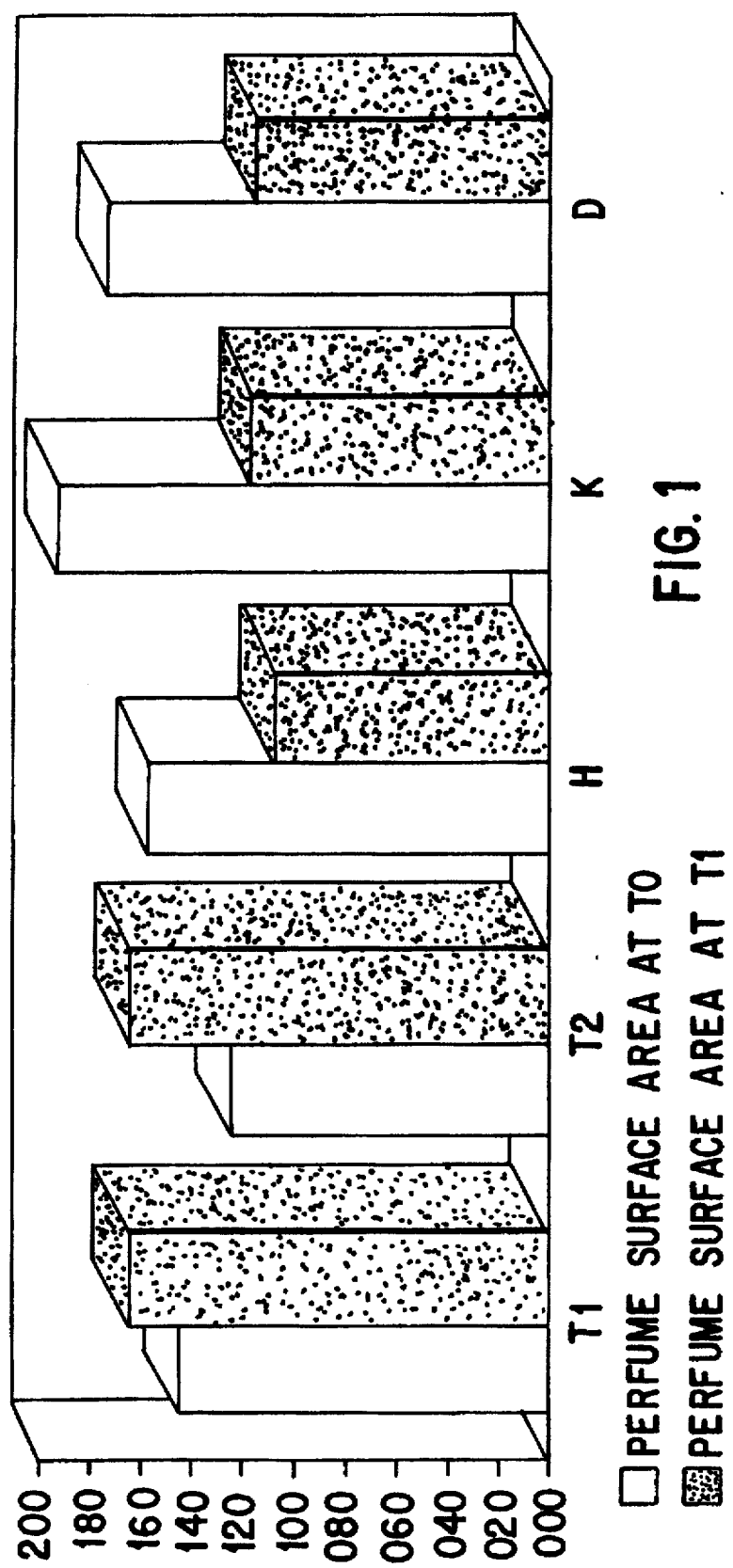
FIG. 1 gives, in the form of histograms, the quantity of perfume evaporated for various compositions, the x-axis denotes the nature of the products and the y-axis denotes the surface area integrated by a calculator, this surface area being expressed in integration unit (arbitrary unit), FIGS. 2 to 5 give the curves showing the natural evaporation of the perfume for various compositions; the x-axis represents the time in minutes and the y-axis the concentration of volatile compounds evaporated in arbitrary units; the curves of FIGS. 2 and 3 are established at time T0 and those of FIGS. 4 and 5 are established after storing the compositions in the open air for one and two days respectively.

The non-film-forming and/or non-thickening plant extract may be selected from the group consisting of fucus, lichen, borage, almond, marshmallow and linseed extracts, and mixtures thereof.

The plant gum may be preferably a polysaccharide gum. This may be selected from the group consisting of xanthan, guar, alginate, alga, cellulose, agar or carob gum.

Preferably, the plant compound is mucilage (a mixture of xanthan gum and the extracts mentioned above).

The plant compound of the present invention (i.e. a non-film-forming and/or non-thickening plant extract or a plant gum) may be obtained by conventional methods known to those of ordinary skill in the art.

The perfume-fixing agent may be chosen in a quantity ranging from 0.05% to 10% by weight relative to the total weight of the composition and is preferably from 0.1 to 3% by weight relative to the total weight of the composition.

The composition may, in addition, comprise one or more organic solvents such as (silicone) oils, alcohols such as ethanol but also propanol, isopropanol, glycols and generally alcohols having 2 to 8 carbon atoms.

The presence of solvent in a perfumed composition allows the massive release of the top note by evaporation of the solvent. Yet it is preferable that the latter is present in a small quantity in order to avoid this top note releasing all at once a quantity of perfume which is too large.

The presence of a plant compound as perfume-fixing agent in the composition makes it possible to prolong the duration of emission of the perfume during the use of this perfumed composition and consequently to prolong the duration of the base note.

Thus, for a perfumed composition to have a correct top note and a sufficient base note, it is desirable to have a balance between the quantities by weight of solvent and of perfume-fixing agent.

Suitable perfumes, include those compounds and extracts known to those of ordinary skill in the art, and may be obtained by conventional methods known to those of ordinary skill in the art.

This ratio of solvent to perfume-fixing agent by weight may be between 0.5 and 10 and may be preferably from 1 to 3 and for example, 2.

It is also desirable to have a ratio by weight between the perfume and the perfume-fixing agent ranging from 0.5 to 50 and preferably from 1 to 30.

The composition according to the invention also comprises at least one carrier compound selected from the carriers conventionally used in the cosmetic and/or dermatological field. It may, in addition, contain one or more active agents which are conventionally used in these fields, gelling agents, preservatives, fillers, emulsifiers.

Thus, the composition according to the invention may be provided in the form of an oil-in-water or water-in-oil (O/W or W/O) emulsion, a gel or a solution. Suitable compositions may be prepared by conventional methods known to those of ordinary skill in the art.

In a preferred embodiment, the plant compound is not hyaluronic acid or a salt thereof.

In a preferred embodiment, the plant extract is not derived from the inner skin of an orange.

In a preferred embodiment, the perfume is not encapsulated by the plant extract.

In particular, the composition according to the invention may be provided in the form of a treatment cream, a cleaning lotion, a mascara, or a foundation.

The present invention also related to a method for fixing and/or prolonging release of a perfume in a cosmetic composition intended for cleaning the skin with a plant compound, the plant compound comprising at least one non-film-forming and/or non-thickening plant extract and at least one plant gum.

The subject of the invention is also a method for fixing and/or prolonging release of a perfume in a cosmetic composition intended for cleaning the skin with a plant compound, the said plant compound comprising at least one plant extract selected from the group consisting of fucus, lichen, borage, almond, marshmallow and linseed extracts and mixtures thereof.

The present invention is also directed to a cosmetic and/or dermatological composition comprising a perfume and at least one non-thickening and/or non-film-forming plant extract and at least one plant gum.

The present invention is also directed to a cosmetic and/or dermatological composition comprising a perfume and a plant compound comprising at least one plant extract selected from the group consisting of fucus, lichen, borage, almond, marshmallow, linseed extracts and mixtures thereof.

Having generally described this invention, a further understanding can be obtained by reference to certain specific examples which are provided herein for purposes of illustration only and are not intended to be limiting unless otherwise specified.

The examples of composition below are given by way of illustration and are non-limitative and the quantities thereof are given in percentage by weight.

| Example | | |
|---|---|---|
| Fatty phase | | |
| paraffin oil | | 8 |
| silicone oil (solvent) | | 6 |
| Emulsifier | | |
| nonionic surfactant | | 3 |
| Aqueous phase | | |
| mucilage | | 3 |
| glycerin | | 3 |
| preservative | | 0.6 |
| gelling agent | | 0.35 |
| UV-screening agent | | 0.05 |
| perfume | | 4.5 |
| water | qs | 100 |

The milk obtained is an oil-in-water emulsion. It is a shower milk for cleaning the body. This milk releases perfume during its use and continues to release it for several hours after application to the skin.

First Comparative Study

The aim of this first study is to show the stable effect of the perfume in a composition according to the invention. It is performed by comparing the emission of perfume from the following different perfumed compositions:

compositions T1 and T2 are compositions according to the invention containing ethanol (0.5%), a perfume (4.5%) and mucilage (3%);

composition H is a composition without perfume-fixing agent, containing a perfume (4.5%) and ethanol (0.5%);

composition K is a composition without solvent, containing a perfume (4.5%) and xanthan gum (0.009%);

composition D is a composition with only perfume (4.5%).

This study was carried out by means of a "Desorption—Concentration—Introduction" (DCI) type chromatograph such as platinum DCI from the company DESLY. It is a system which makes it possible to make samples of volatile compounds in a chromatograph. This apparatus performs dynamic measurements of vapor pressure differences. These measurements are performed in a few hours and depend on the room temperature and the level of humidity in the atmosphere. They are plotted in FIG. 1. This figure shows the various values for the calculation of the surface area for the various compositions at the times T0 and T1.

300 µl samples are incorporated into stainless steel boats. The measurement taken at time T0 (FIG. 1) correspond to an evaporation for 5 minutes at ambient temperature, and those taken at time T1 (FIG. 1), to a controlled evaporation for 1 h 30 min at 40° C. in a ventilated oven. The trapping time, or the measuring time, for the samples at T0 is 1 minute, and 5 minutes at T1. The time of 5 min at T1 makes it possible to have a relative reading as concentration of the volatile compounds.

For each sample, the quantity of the principal constituents of the vapor phase, which are trapped at time T0 and at time T1, is recorded.

The following results are obtained from FIG. 1.

The emission of perfume at T0 for compositions T1 and T2 is slightly less than that of compositions H, K and D. This is due to a higher initial evaporation of the perfume (top note) for H, K and D than for T. This shows the retention effect of the plant compound with respect to the perfume.

Next at time T1, the emission of the complete perfume (medium note and final note) in compositions T1 and T2 is greater than that of formulas H, K and D. This shows the stable effect of the perfume in the composition according to the invention which comprises a plant compound as perfume-fixing agent.

Indeed, the compositions which do not contain a perfume-fixing agent (H, K and D) emit at T1 quantitatively much less perfume that those containing it. The top note which was very high at the beginning, at T0 for H, K and D, therefore reduced the emission of the medium note and, even more, that of the final note.

Second Comparative Study

This second study, which confirms the results of the first, is performed by means of an "Alabaster" type olfactometer. It is a system equipped with a monosensor having a semiconductor (metal oxide $SnO_2$). This study uses the same compositions T1, H, K and D as the first study.

This apparatus makes it possible to quantitatively measure the natural evaporation, at room temperature, of the volatile compounds of each composition. This measurement is performed over a period of 30 minutes in an insulated chamber.

The results obtained are presented in FIGS. 2, 3, 4 and 5.

The curves of these figures represent, for each composition, the evaporated quantity in arbitrary unit of the total volatile compounds, over 30 minutes.

Figure 2:
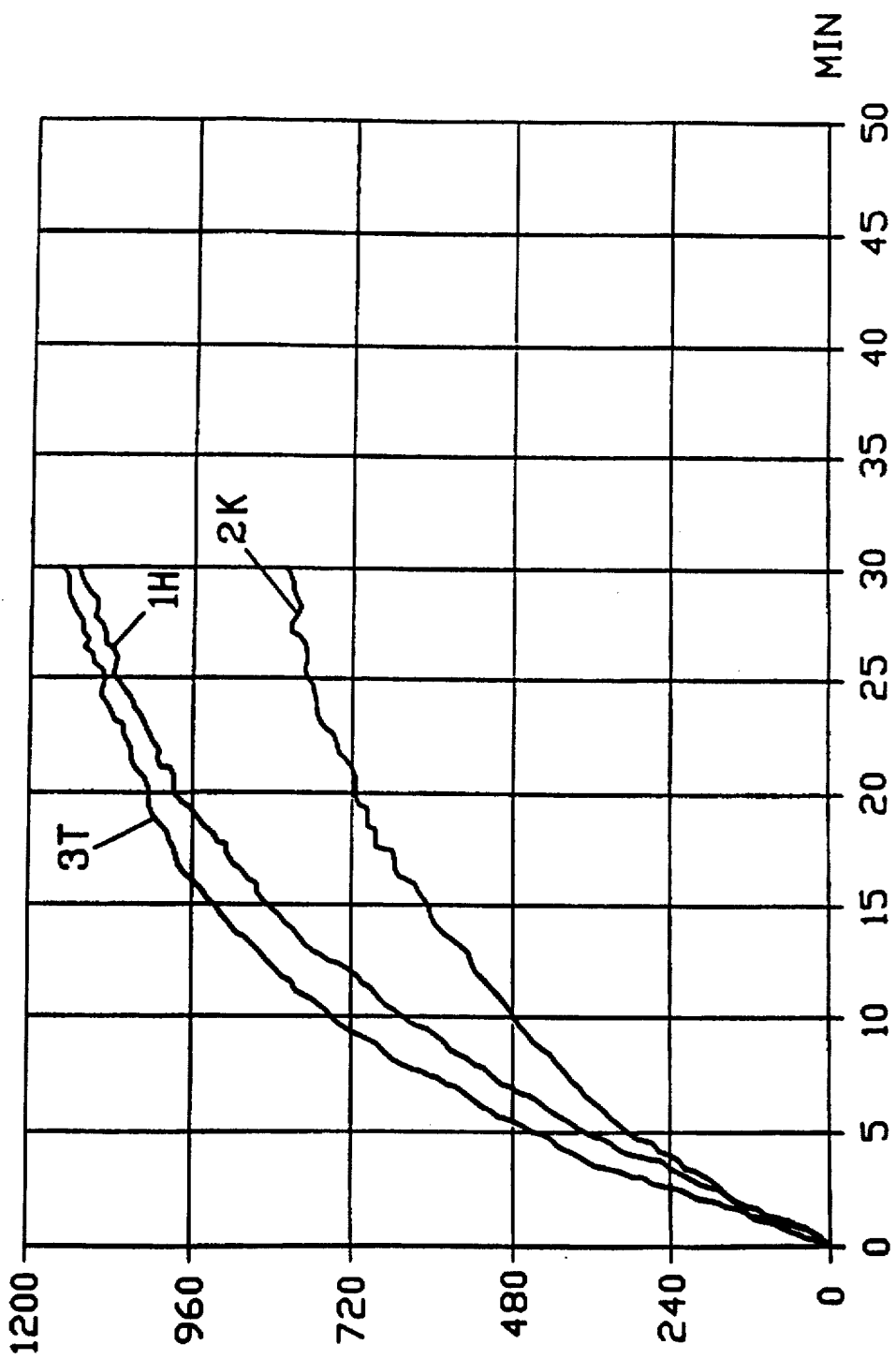
Figure 3:
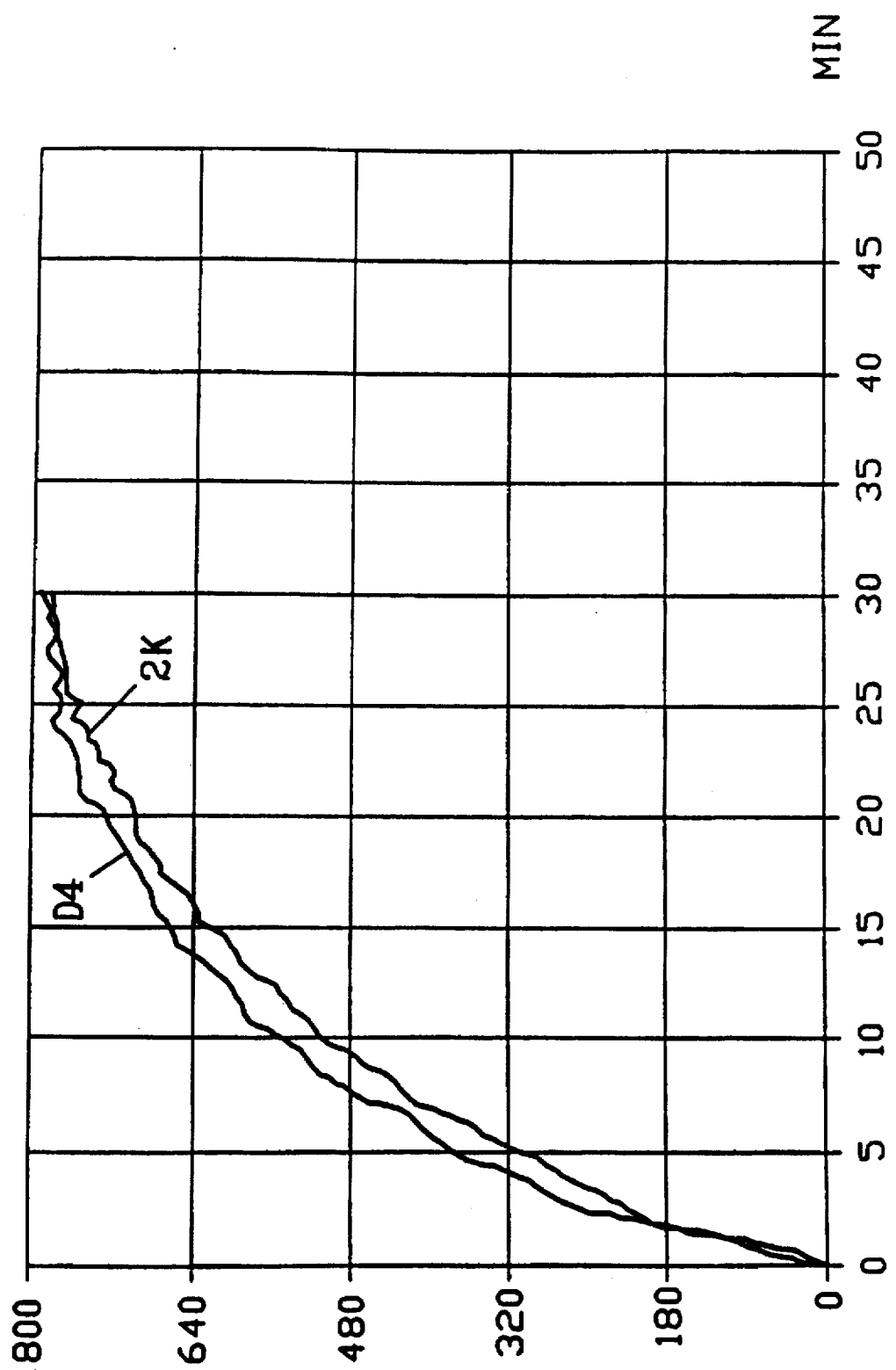
Figure 4:
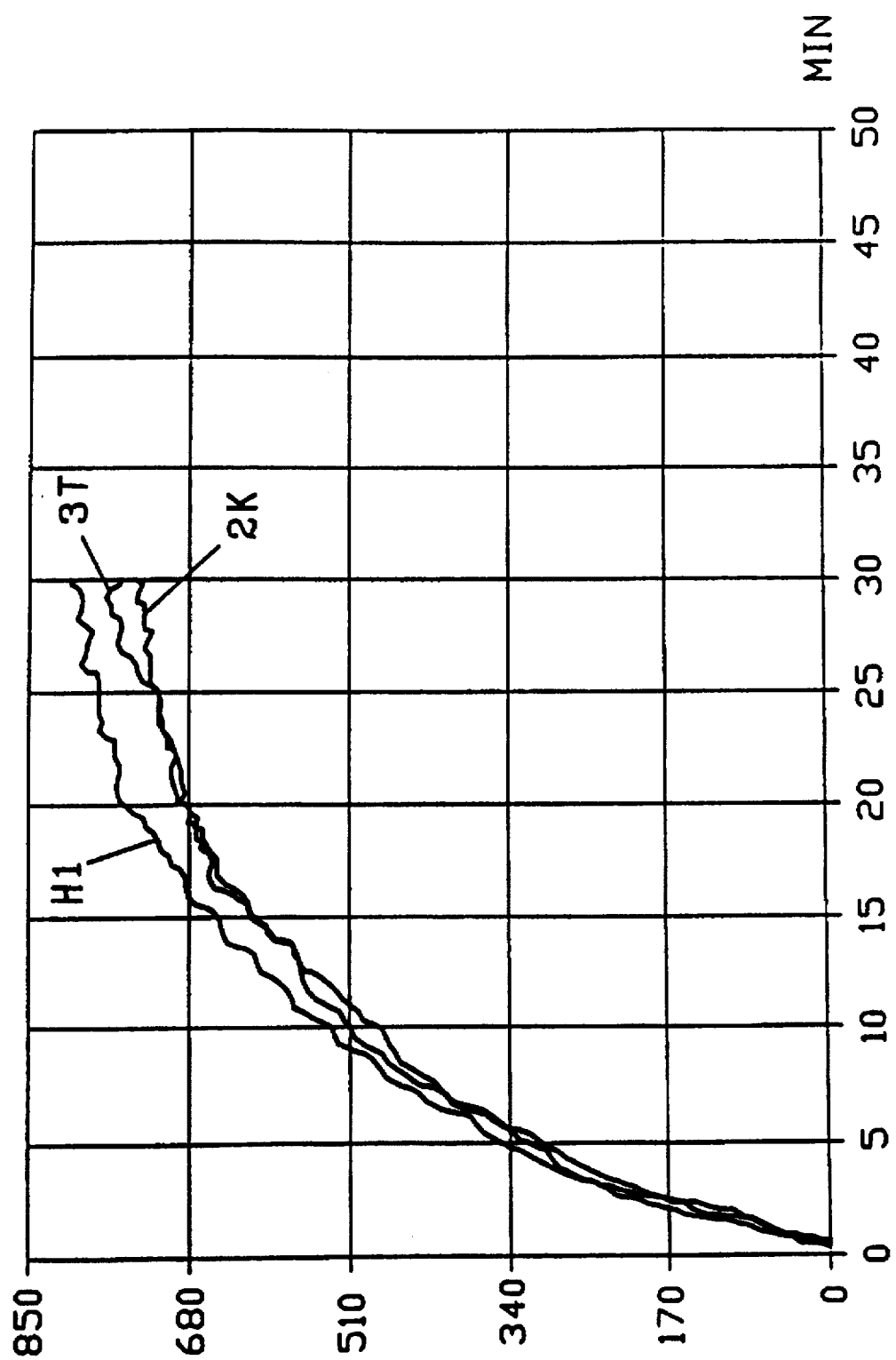
Figure 5:
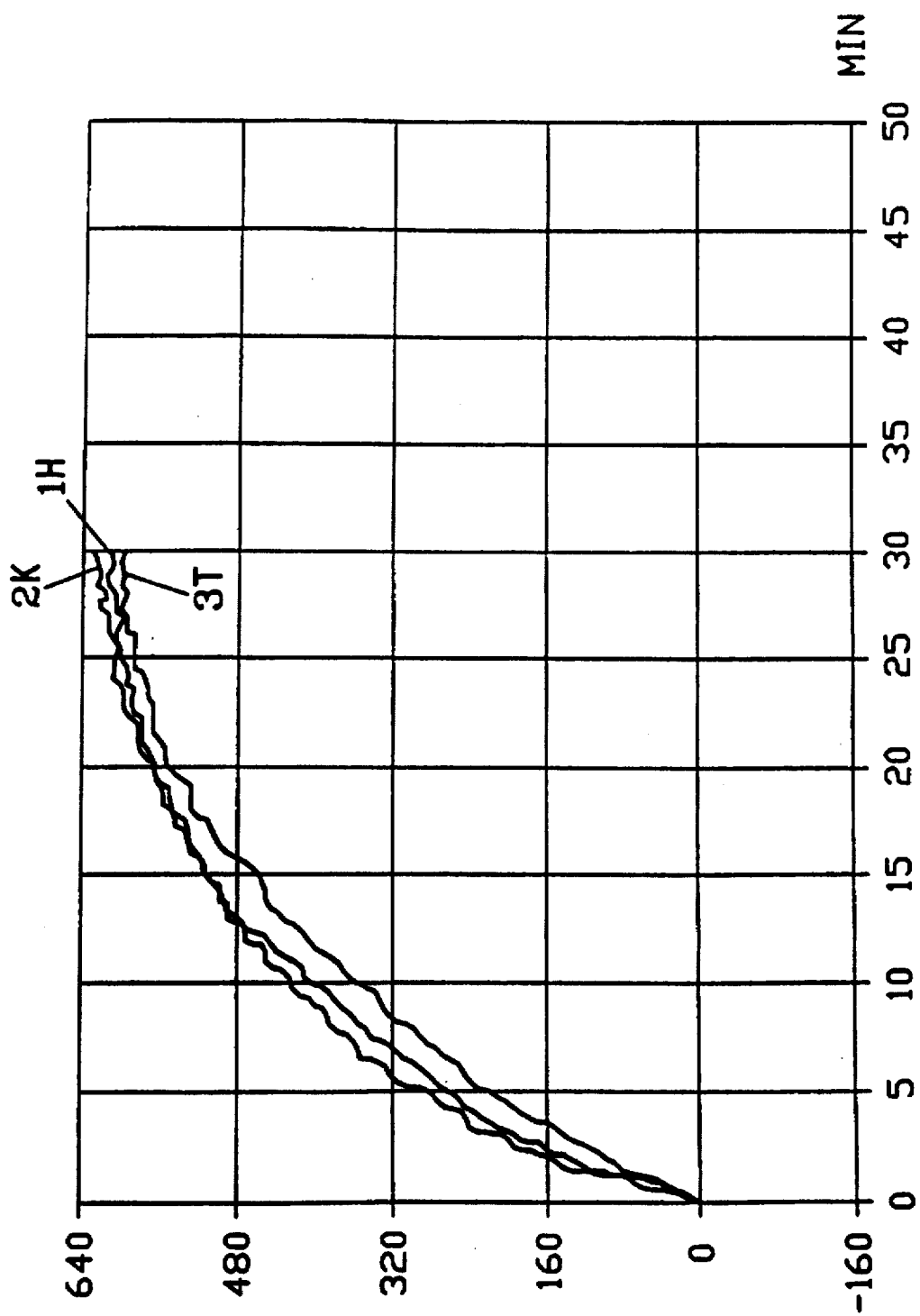

FIGS. 2 and 3 present the evaporation curves for the volatile compounds of the compositions at time T=0. FIGS. 4 and 5 present the evaporation curves for the volatile compounds of the compositions, after storing in the open air for one and two days respectively.

For each figure, curve 1 represents the evaporation of the volatile compounds of composition H, curve 2 that of the volatile compounds of composition K, curve 3 that of the volatile compounds of composition T and curve 4 that of the volatile compounds of composition D. It should be noted that in this type of curves, the greater the slope of the origin, the less stable the perfume.

FIG. 2 indeed shows that at time T=0, composition K (without solvent but with xanthan gum) contains considerably fewer volatile compounds compared with the other compositions T and H. This is due to the fact that these last two compositions contain more solvent than compositions K.

Composition T first emits more volatile compounds than composition H (greater slope). After 30 min, the phenomenon decreases and extrapolation of the curves shows that there is a perfume-retaining effect in composition T since curve 1 passes above curve 3.

Moreover, FIG. 3 shows at T0 that the evaporation of the volatile compounds of compositions K and D are comparable and very low. This shows that the gum present in the composition plays no role at T0 in the evaporation of the perfume.

FIG. 4 shows that the slope of composition T is smaller than that of composition H. After 30 min, the curves become closer and extrapolation shows that curve 3 (composition T) will pass above curve 1 (composition H) and therefore that after a certain time, the emission of perfume from composition T will be greater than that from composition H.

The perfume-fixing agent first acts as an agent for limiting evaporation of perfume, and then allows the perfume to be released over time. This is shown in FIGS. 2 and 5.

By comparing the curves in FIG. 5 with each other, it is observed that composition H and K while remaining at a sufficient level for detection by the nose, which is consistent with a greater stability of the perfume for composition T than for compositions K and H. The emission of perfume after two days of storage from compositions H and K, and consequently the total quantity of perfume evaporated, is greater than that from T (same analysis as for FIG. 4 with a smaller gap between the curves because of the fact that the volatile compounds decrease over time; it becomes difficult to measure them).

Consequently, in spite of a high evaporation of perfume at T0 by the composition T of the invention, the emission of perfume extends over time up to more than two days, and this in a detectable manner "olfactively" speaking.

On comparing the curves in FIGS. 4 and 5 with those in FIG. 2, it is observed that the emission of volatile compounds after one and two days is lower than that of the volatile compounds at T0 (respective limiting values, 840 and 630 instead of 1150)

The emission of perfume from compositions H and T, after two days, comes to the same level as that from composition K to T0, which is consistent with the presence of a large quantity of perfume.

Furthermore, the role of the solvent became negligible in the emission of perfume after one and then two days of storage.

Obviously, additional modifications and variations of the present invention are possible in light of the above teachings. It is therefore to be understood that within the scope of the appended claims, the invention may be practiced otherwise than as specifically described herein.

This application is based on French Patent Application 94-10764, filed with the French Patent Office on Sep. 8, 1994, the entire contents of which are hereby incorporated by reference.

What is claimed is new and is desired to be secured by Letters Patent of the United States is:

1. A method for fixing and/or prolonging release of a perfume in a cosmetic and/or dermatological composition which comprises incorporating a plant compound into a cosmetic comprising a perfume wherein said plant compound comprises at least one non-thickening and/or non-film-forming plant extract selected from the group consisting of fucus, lichen, borage, almond, marshmallow and linseed extracts and mixtures thereof, and at least one plant gum.

2. The method of claim 1, wherein said plant gum is a polysaccharide gum.

3. The method of claim 1, wherein the plant gum is xanthan gum.

4. A method for fixing and/or prolonging release of a perfume in a cosmetic and/or dermatological composition comprising incorporating a plant compound into a cosmetic comprising a perfume wherein said plant compound comprises at least one plant extract selected from the group consisting of fucus, lichen, borage, almond, marshmallow and linseed extracts and mixtures thereof.

5. The method of claim 1, wherein said plant compound is mucilage.

6. The method of claim 1, wherein said composition further comprises at least one volatile solvent selected from the group consisting of ethanol, isopropanol, glycols.

7. The method of claim 6, wherein the ratio by weight between said volatile solvent and said plant compound ranges from 0.5 to 10.

8. The method of claim 7, wherein the ratio by weight between the volatile solvent and the plant compound is 2.

9. The method of claim 1, wherein the ratio by weight between said perfume and said plant compound ranges from 0.5 to 50.

10. The method of claim 1, wherein said plant compound is present in a quantity ranging from 0.05 to 10% by weight relative to the total weight of said composition.

11. The method of claim 1, wherein said plant compound is present in a quantity ranging from 0.1 to 3% by weight relative to the total weight of said composition.

12. The method of claim 1, wherein said composition is a composition for cleaning the skin.

13. The method of claim 3, wherein said composition is a composition for cleaning the skin.

14. A cosmetic and/or dermatological composition comprising a perfume and a plant compound, wherein said plant compound comprises at least one non-thickening and/or non-film-forming plant extract selected from the group consisting of fucus, lichen, borage, almond, marshmallow and linseed extracts and mixtures thereof, and at least one plant gum.

15. A cosmetic and/or dermatological composition comprising a perfume and a plant compound, wherein said plant compound comprises at least one plant extract selected from the group consisting of fucus, lichen, borage, almond, marshmallow and linseed extracts and mixtures thereof.

16. A cosmetic and/or dermatological composition comprising a perfume and a plant compound obtained by the steps comprising incorporating a plant compound into a cosmetic comprising a perfume wherein said plant compound comprises at least one non-thickening and/or non-film-forming plant extract selected from the group consisting of fucus, lichen, borage, almond, marshmallow and linseed extracts and mixtures thereof, and at least one plant gum.

* * * * *